US008846988B2

(12) United States Patent  
Jevtic et al.

(10) Patent No.: US 8,846,988 B2  
(45) Date of Patent: Sep. 30, 2014

(54) LIQUID ESTERIFICATION FOR THE PRODUCTION OF ALCOHOLS

(75) Inventors: Radmila Jevtic, Pasadena, TX (US); Victor Johnston, Houston, TX (US); Lincoln Sarager, Houston, TX (US); R. Jay Warner, Houston, TX (US); Heiko Weiner, Pasadena, TX (US); Trinity Horton, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 95 days.

(21) Appl. No.: 13/094,488

(22) Filed: Apr. 26, 2011

(65) Prior Publication Data

US 2012/0010437 A1    Jan. 12, 2012

Related U.S. Application Data

(60) Provisional application No. 61/363,056, filed on Jul. 9, 2010.

(51) Int. Cl.
*C07C 29/12* (2006.01)
*C07C 67/08* (2006.01)
*C07C 29/88* (2006.01)
*C07C 29/141* (2006.01)
*C07C 29/90* (2006.01)
*C07C 29/149* (2006.01)

(52) U.S. Cl.
CPC .............. *C07C 29/141* (2013.01); *C07C 67/08* (2013.01); *C07C 29/88* (2013.01); *C07C 29/90* (2013.01); *C07C 29/149* (2013.01)
USPC ............ 568/890; 568/881; 568/884; 568/885

(58) Field of Classification Search
None
See application file for complete search history.

(56) References Cited

U.S. PATENT DOCUMENTS

| | | |
|---|---|---|
| 1,939,116 A | 12/1933 | Fuchs |
| 2,607,807 A | 8/1952 | Ford |
| 2,649,407 A | 8/1953 | Harrison et al. |
| 2,702,783 A | 2/1955 | Harrison et al. |
| 2,744,939 A | 5/1956 | Kennel |
| 2,801,209 A | 7/1957 | Muller et al. |
| 2,859,241 A | 11/1958 | Schnizer |
| 2,882,244 A | 4/1959 | Milton |
| 3,102,150 A | 8/1963 | Hunter et al. |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,769,329 A | 10/1973 | Paulik et al. |
| 3,772,380 A | 11/1973 | Paulik et al. |
| 3,847,756 A | 11/1974 | Statman et al. |
| 3,864,284 A | 2/1975 | Clippinger et al. |
| 3,990,952 A | 11/1976 | Katzen et al. |
| 4,126,539 A | 11/1978 | Derr, Jr. et al. |
| 4,149,940 A | 4/1979 | Pinto |
| 4,275,228 A | 6/1981 | Gruffaz et al. |
| 4,306,942 A | 12/1981 | Brush et al. |
| 4,308,131 A | 12/1981 | Bannon |
| 4,317,918 A | 3/1982 | Takano et al. |
| 4,319,058 A | 3/1982 | Kulpranthipanja et al. |
| 4,338,221 A | 7/1982 | Qualeatti |
| 4,352,940 A | 10/1982 | Adelman et al. |
| 4,370,491 A | 1/1983 | Bott et al. |
| 4,379,028 A | 4/1983 | Berg et al. |
| 4,395,576 A | 7/1983 | Kwantes et al. |
| 4,398,039 A | 8/1983 | Pesa et al. |
| 4,421,939 A | 12/1983 | Kiff et al. |
| 4,422,903 A | 12/1983 | Messick et al. |
| 4,443,639 A | 4/1984 | Pesa et al. |
| 4,454,358 A | 6/1984 | Kummer et al. |
| 4,456,775 A | 6/1984 | Travers et al. |
| 4,463,138 A | 7/1984 | Wu et al. |
| 4,465,854 A | 8/1984 | Pond et al. |
| 4,465,875 A | 8/1984 | Greenbank et al. |
| 4,471,136 A | 9/1984 | Larkins et al. |
| 4,476,326 A | 10/1984 | Lin et al. |
| 4,480,115 A | 10/1984 | McGinnis |
| 4,481,146 A | 11/1984 | Leupold et al. |
| 4,492,808 A | 1/1985 | Hagen et al. |
| 4,497,967 A | 2/1985 | Wan |
| 4,517,391 A | 5/1985 | Schuster et al. |
| 4,520,213 A | 5/1985 | Victor |
| 4,541,897 A | 9/1985 | Sommer et al. |
| 4,559,109 A | 12/1985 | Lee et al. |

(Continued)

FOREIGN PATENT DOCUMENTS

| CN | 201768393 | 3/2011 |
|---|---|---|
| CN | 102228831 | 11/2011 |

(Continued)

OTHER PUBLICATIONS

Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Subramani et al. "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

Santori et al.(2000). Hydrogenation of carbonylic compounds on Pt/SiO2 catalysts modified with SnBu4, Studies in Surface Science and Catalysis, 130, 2063-2068.

(Continued)

*Primary Examiner* — Sudhakar Katakam

(57) ABSTRACT

Purifying and/or recovery of ethanol from a crude ethanol product obtained from the hydrogenation of acetic acid. Separation and purification processes of crude ethanol mixture are employed to allow recovery of ethanol and remove impurities. In addition, the process involves returning acetaldehyde separated from the crude ethanol product to the reactor.

22 Claims, 3 Drawing Sheets

(56) References Cited

U.S. PATENT DOCUMENTS

| | | |
|---|---|---|
| 4,569,726 A | 2/1986 | Berg et al. |
| 4,611,085 A | 9/1986 | Kitson |
| 4,626,321 A | 12/1986 | Grethlein et al. |
| 4,628,130 A | 12/1986 | Bournonville et al. |
| 4,678,543 A | 7/1987 | Houben et al. |
| 4,692,218 A | 9/1987 | Houben et al. |
| 4,751,334 A | 6/1988 | Turner et al. |
| 4,774,365 A | 9/1988 | Chen et al. |
| 4,777,303 A | 10/1988 | Kitson et al. |
| 4,804,791 A | 2/1989 | Kitson et al. |
| 4,826,795 A | 5/1989 | Kitson et al. |
| 4,842,693 A | 6/1989 | Wheldon |
| 4,843,170 A | 6/1989 | Isshiki et al. |
| 4,886,905 A | 12/1989 | Larkins et al. |
| 4,908,477 A | 3/1990 | Hartmann et al. |
| 4,961,826 A | 10/1990 | Grethlein et al. |
| 4,978,778 A | 12/1990 | Isshiki et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,015,786 A | 5/1991 | Araki et al. |
| 5,026,908 A | 6/1991 | Smith et al. |
| 5,035,776 A | 7/1991 | Knapp |
| 5,047,592 A | 9/1991 | Carpenter |
| 5,061,671 A | 10/1991 | Kitson et al. |
| 5,070,016 A | 12/1991 | Hallberg |
| 5,096,592 A | 3/1992 | Schucker |
| 5,124,004 A | 6/1992 | Grethlein et al. |
| 5,144,068 A | 9/1992 | Smith et al. |
| 5,149,680 A | 9/1992 | Kitson et al. |
| 5,185,308 A | 2/1993 | Bartley et al. |
| 5,185,481 A | 2/1993 | Muto et al. |
| 5,196,601 A | 3/1993 | Kitsuki et al. |
| 5,198,592 A | 3/1993 | Van Beijnum et al. |
| 5,215,902 A | 6/1993 | Tedder |
| 5,221,481 A | 6/1993 | Schucker |
| 5,227,141 A | 7/1993 | Kim et al. |
| 5,233,099 A | 8/1993 | Tabata et al. |
| 5,237,108 A | 8/1993 | Marraccini et al. |
| 5,250,271 A | 10/1993 | Horizoe et al. |
| 5,334,751 A | 8/1994 | Lemanski et al. |
| 5,348,625 A | 9/1994 | Berg |
| 5,399,752 A | 3/1995 | Okrasinski et al. |
| 5,414,161 A | 5/1995 | Uhm et al. |
| 5,415,741 A | 5/1995 | Berg |
| 5,416,237 A | 5/1995 | Aubigne et al. |
| 5,426,246 A | 6/1995 | Nagahara et al. |
| 5,437,770 A | 8/1995 | Berg |
| 5,445,716 A | 8/1995 | Berg |
| 5,449,440 A | 9/1995 | Rescalli et al. |
| 5,475,144 A | 12/1995 | Watson et al. |
| 5,476,827 A | 12/1995 | Ferrero et al. |
| 5,476,974 A | 12/1995 | Moore et al. |
| 5,488,185 A | 1/1996 | Ramachandran et al. |
| 5,502,248 A | 3/1996 | Funk et al. |
| 5,527,969 A | 6/1996 | Kaufhold et al. |
| 5,565,068 A | 10/1996 | Parker et al. |
| RE35,377 E | 11/1996 | Steinberg et al. |
| 5,585,523 A | 12/1996 | Weiguny et al. |
| 5,599,976 A | 2/1997 | Scates et al. |
| 5,719,315 A | 2/1998 | Tustin et al. |
| 5,731,456 A | 3/1998 | Tustin et al. |
| 5,747,486 A | 5/1998 | Sohda et al. |
| 5,762,765 A | 6/1998 | Berg |
| 5,770,761 A | 6/1998 | Lin et al. |
| 5,770,770 A | 6/1998 | Kim et al. |
| 5,800,681 A | 9/1998 | Berg |
| 5,821,111 A | 10/1998 | Grady et al. |
| 5,861,530 A | 1/1999 | Atkins et al. |
| 5,932,764 A | 8/1999 | Morris et al. |
| 5,973,193 A | 10/1999 | Crane et al. |
| 5,993,610 A | 11/1999 | Berg |
| 5,998,658 A | 12/1999 | Wu et al. |
| 6,040,474 A | 3/2000 | Jobson et al. |
| 6,046,127 A | 4/2000 | Mimoun |
| 6,093,845 A | 7/2000 | Van Acker et al. |
| 6,121,498 A | 9/2000 | Tustin et al. |
| 6,143,930 A | 11/2000 | Singh et al. |
| 6,214,253 B1 | 4/2001 | Moore et al. |
| 6,232,352 B1 | 5/2001 | Vidalin et al. |
| 6,294,703 B1 | 9/2001 | Hara et al. |
| 6,326,515 B1 | 12/2001 | Clode et al. |
| 6,339,171 B1 | 1/2002 | Singh et al. |
| 6,342,464 B1 | 1/2002 | Arhancet et al. |
| 6,375,807 B1 | 4/2002 | Nieuwoudt et al. |
| 6,403,840 B1 | 6/2002 | Zhou et al. |
| 6,444,842 B1 | 9/2002 | Gerberich et al. |
| 6,458,996 B1 | 10/2002 | Muskett |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,713,655 B2 | 3/2004 | Yilmaz et al. |
| 6,723,886 B2 | 4/2004 | Allison et al. |
| 6,755,975 B2 | 6/2004 | Vane et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,867,164 B2 | 3/2005 | Obana et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,084,312 B1 | 8/2006 | Huber et al. |
| 7,091,155 B2 | 8/2006 | Inui et al. |
| 7,109,385 B2 | 9/2006 | Tatake et al. |
| 7,115,772 B2 | 10/2006 | Picard et al. |
| 7,208,624 B2 | 4/2007 | Scates et al. |
| 7,223,886 B2 | 5/2007 | Scates et al. |
| 7,226,886 B2 | 6/2007 | Jayaratne et al. |
| 7,297,236 B1 | 11/2007 | Vander Griend et al. |
| 7,351,559 B2 | 4/2008 | Verser et al. |
| 7,399,892 B2 | 7/2008 | Rix et al. |
| 7,425,657 B1 | 9/2008 | Elliott et al. |
| 7,507,562 B2 | 3/2009 | Verser et al. |
| 7,553,397 B1 | 6/2009 | Colley et al. |
| 7,572,353 B1 | 8/2009 | Vander Griend |
| 7,594,981 B2 | 9/2009 | Ikeda |
| 7,601,865 B2 | 10/2009 | Verser et al. |
| 7,608,744 B1 | 10/2009 | Johnston et al. |
| 7,652,167 B2 | 1/2010 | Miller et al. |
| 7,667,068 B2 | 2/2010 | Miller et al. |
| 7,678,940 B2 | 3/2010 | Miura et al. |
| 7,682,812 B2 | 3/2010 | Verser et al. |
| 7,700,814 B2 | 4/2010 | Garton et al. |
| 7,718,039 B2 | 5/2010 | Dirkzwager et al. |
| 7,732,173 B2 | 6/2010 | Mairal et al. |
| 7,744,727 B2 | 6/2010 | Blum et al. |
| 7,834,223 B2 | 11/2010 | Atkins et al. |
| 7,834,708 B1 | 11/2010 | Ren |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 7,906,680 B2 | 3/2011 | Scates et al. |
| 7,947,746 B2 | 5/2011 | Daniel et al. |
| 8,071,821 B2 | 12/2011 | Johnston et al. |
| 2003/0013908 A1 | 1/2003 | Horan et al. |
| 2003/0077771 A1 | 4/2003 | Verser et al. |
| 2003/0078456 A1 | 4/2003 | Yilmaz et al. |
| 2003/0120121 A1 | 6/2003 | Sherman et al. |
| 2003/0135069 A1 | 7/2003 | Fujita et al. |
| 2004/0152915 A1 | 8/2004 | Fujita et al. |
| 2004/0242917 A1 | 12/2004 | Inui et al. |
| 2005/0176996 A1 | 8/2005 | Law et al. |
| 2005/0197506 A1 | 9/2005 | Scates et al. |

(56) References Cited

U.S. PATENT DOCUMENTS

| | | |
|---|---|---|
| 2006/0019360 A1 | 1/2006 | Verser et al. |
| 2006/0106246 A1 | 5/2006 | Warner et al. |
| 2006/0127999 A1 | 6/2006 | Verser et al. |
| 2006/0224013 A1 | 10/2006 | Inui et al. |
| 2006/0252956 A1 | 11/2006 | Miller et al. |
| 2007/0031954 A1 | 2/2007 | Mairal et al. |
| 2007/0138083 A1 | 6/2007 | Aizawa |
| 2007/0270511 A1 | 11/2007 | Melnichuk et al. |
| 2008/0135396 A1 | 6/2008 | Blum |
| 2008/0193989 A1 | 8/2008 | Verser et al. |
| 2008/0207953 A1 | 8/2008 | Houssin et al. |
| 2008/0207959 A1 | 8/2008 | Plante et al. |
| 2009/0005588 A1 | 1/2009 | Hassan et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey et al. |
| 2009/0221725 A1 | 9/2009 | Chorney et al. |
| 2009/0270651 A1 | 10/2009 | Zinobile et al. |
| 2009/0281354 A1 | 11/2009 | Mariansky et al. |
| 2009/0299092 A1 | 12/2009 | Beavis et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0121119 A1 | 5/2010 | Sherman et al. |
| 2010/0130775 A1 | 5/2010 | Voss et al. |
| 2010/0137630 A1 | 6/2010 | Garton et al. |
| 2010/0185021 A1 | 7/2010 | Ross et al. |
| 2010/0197485 A1 | 8/2010 | Johnston et al. |
| 2010/0197959 A1 | 8/2010 | Johnston et al. |
| 2010/0197985 A1 | 8/2010 | Johnston et al. |
| 2010/0204512 A1 | 8/2010 | Kimmich et al. |
| 2010/0273229 A1 | 10/2010 | Verser et al. |
| 2011/0004033 A1 | 1/2011 | Johnston et al. |
| 2011/0034741 A1 | 2/2011 | Sherman et al. |
| 2011/0046421 A1* | 2/2011 | Daniel et al. ............ 568/885 |
| 2011/0082322 A1 | 4/2011 | Jevtic et al. |
| 2011/0185628 A1 | 8/2011 | Johnston et al. |
| 2011/0190547 A1 | 8/2011 | Jevtic et al. |
| 2011/0190548 A1 | 8/2011 | Jevtic et al. |
| 2011/0190551 A1 | 8/2011 | Jevtic et al. |
| 2011/0224462 A1 | 9/2011 | Ditzel et al. |
| 2011/0275861 A1 | 11/2011 | Johnston et al. |
| 2011/0275862 A1 | 11/2011 | Johnston et al. |
| 2012/0010437 A1 | 1/2012 | Jevtic et al. |
| 2012/0010438 A1 | 1/2012 | Lee et al. |
| 2012/0010439 A1 | 1/2012 | Jevtic |
| 2012/0010440 A1 | 1/2012 | Sarager |
| 2012/0010445 A1 | 1/2012 | Johnston et al. |
| 2012/0273338 A1 | 11/2012 | Lee et al. |
| 2012/0277481 A1 | 11/2012 | Warner et al. |

FOREIGN PATENT DOCUMENTS

| | | |
|---|---|---|
| CN | 102229520 | 11/2011 |
| EP | 0056488 | 7/1982 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0400904 | 5/1990 |
| EP | 0372847 | 6/1990 |
| EP | 0456647 | 11/1991 |
| EP | 0944572 | 9/1999 |
| EP | 0990638 | 4/2000 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 1-268654 | 10/1989 |
| JP | 4-193304 | 7/1992 |
| JP | 6-116182 | 4/1994 |
| JP | 2001-046874 | 2/2001 |
| JP | 2003-093827 | 4/2003 |
| WO | WO 82/03854 | 11/1982 |
| WO | WO 83/03409 | 10/1983 |
| WO | WO 98/25876 | 6/1998 |
| WO | WO 02/092541 | 11/2002 |
| WO | WO 2005/044783 | 5/2005 |
| WO | WO 2005/102513 | 11/2005 |
| WO | WO 2007/003897 | 1/2007 |
| WO | WO 2007/107371 | 9/2007 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | WO 2009/048335 | 4/2009 |
| WO | WO 2009/063174 | 5/2009 |
| WO | WO 2009/063176 | 5/2009 |
| WO | WO 2009/077719 | 6/2009 |
| WO | WO 2009/077729 | 6/2009 |
| WO | WO 2009/086839 | 7/2009 |
| WO | WO 2009/105860 | 9/2009 |
| WO | WO 2010/014145 | 2/2010 |
| WO | WO 2010/014148 | 2/2010 |
| WO | WO 2010/014151 | 2/2010 |
| WO | WO 2010/014153 | 2/2010 |
| WO | WO 2010/030320 | 3/2010 |
| WO | WO 2010/055285 | 5/2010 |
| WO | WO 2011/053365 | 5/2011 |
| WO | WO 2011/097193 | 8/2011 |
| WO | WO 2011/097219 | 8/2011 |
| WO | WO 2011/097220 | 8/2011 |
| WO | WO 2011/097222 | 8/2011 |
| WO | WO 2011/097227 | 8/2011 |
| WO | WO 2011/140460 | 11/2011 |
| WO | WO 2012/006219 | 1/2012 |
| WO | WO 2012/006228 | 1/2012 |
| WO | WO 2012/006499 | 1/2012 |

OTHER PUBLICATIONS

Rachmady, Acetic Acid Reduction by H2 on Bimetallic Pt—Fe Catalysts, Journal of Catalysis 209, 87-98 (Apr. 1, 2002), Elsevier Science (USA).

Perry et al., "Perry's Chemical Engineer's Handbook", 7th Edition (1997) pp. 22-37 and 22-69.

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Burkhanov et al., "Palladium-Based Alloy Membranes for Separation of High Purity Hydrogen from Hydrogen-Containing Gas Mixtures", Platinum Metals Rev., 2011, 55, (1), pp. 3-12.

Baker et al., "Membrane separation systems: recent developments and future directions", (1991) pp. 151-169.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

(56) References Cited

OTHER PUBLICATIONS

International Search Report and Written Opinion for PCT/US2010/054136 mailed May 25, 2011.
Written Opinion mailed Mar. 16, 2012 in corresponding International Application No. PCT/US2010/054136.
Written Opinion mailed May 8, 2012 in corresponding International Application No. PCT/US2011/023332.
International Preliminary Report on Patentability mailed Jun. 25, 2012 in corresponding International Application No. PCT/US2011/023332.
International Search Report for PCT/US2011/023269 mailed Aug. 5, 2011.
International Written Opinion mailed May 8, 2012 in corresponding International Application No. PCT/US2011/023269.
International Preliminary Report on Patentability mailed Jun. 27, 2012 in corresponding International Application No. PCT/US2011/023269.
International Search Report mailed Mar. 29, 2012 in corresponding International Application No. PCT/US2011/046508.
International Search Report and Written Opinion mailed Feb. 2, 2012 in corresponding International Application No. PCT/US2011/046508.
International Search Report and Written Opinion mailed Oct. 14, 2011 in corresponding International Application No. PCT/US2011/046503.
International Search Report and Written Opinion mailed Sep. 2, 2011 in corresponding International Application No. PCT/US2011/023276.
Written Opinion mailed May 8, 2012 in corresponding International Application No. PCT/US2011/023276.
International Preliminary Report on Patentability mailed Jun. 27, 2012 in corresponding International Application No. PCT/US2011/023276.
International Search Report and Written Opinion mailed Oct. 12, 2011 in corresponding International Application No. PCT/US2011/035543.
Witzeman and Agreda in "Acetic Acid and its Derivatives,", Marcel Dekker, NY, 1992, p. 271.
J. Jones, et al., "The Cativa™ Process for the Manufacture of Acetic Acid", Platinum Metals Review, vol. 44, No. 3, pp. 94-104 (Jul. 2000).
International Search Report and Written Opinion mailed Jul. 6, 2012 in corresponding International Application No. PCT/US2011/059889.
International Search Report and Written Opinion mailed Sep. 19, 2012 in corresponding International Application No. PCT/US2011/059882.
Marian Simo et al., "Adsorption/Desorption of Water and Ethanol on 3A Zeolite in Near-Adiabatic Fixed Bed", Ind. Eng. Chem. Res., 2009, 48, 9247-9260.
Hidetoshi Kita et al., "Synthesis of a zeolite NaA membrane for pervaporation of water/organic liquid mixtures", Journal of Materials Science Letters, 14 (1995) 206-208.
Yu Huang et al., "Low-Energy Distillation-Membrane separation Process" Industrial & Engineering Chemistry Research, American Chemical Society, US, vol. 49, No. 8, Jan. 1, 2010, pp. 3760-3768, XP 002657719.
International Search Report and Written Opinion mailed Aug. 2, 2012 in corresponding International Application No. PCT/US2012/035220.
International Search Report and Written Opinion mailed Feb. 23, 2012 in corresponding International Application No. PCT/US2011/042646.
Written Opinion mailed Jul. 9, 2012 in corresponding International Application No. PCT/US2011/042646.
International Preliminary Report on Patentability mailed Sep. 26, 2012 in corresponding International Application No. PCT/US2011/042646.
International Search Report and Written Opinion mailed Jul. 30, 2012 in corresponding International Application No. PCT/US2012/035189.
International Search Report and Written Opinion mailed Jul. 11, 2012 in corresponding International Application No. PCT/US2012/035182.
International Search Report and Written Opinion mailed Aug. 6, 2012 in corresponding International Application No. PCT/US2012/035196.
Anonymous, "Studies in Extractive and Azeotropic Distillation Series: Study No. 4—Separation of Alcohols from the Acetate/Alcohol/Water Ternary by Extractive Distillation", May 9, 2008, pp. 1-9.
V. Ragaini et al., "Increasing the value of dilute acetic acid streams through esterification Part 1. Experimental analysis of the reaction zone", Applied Catalysis B: Environmental, vol. 64, 2006, pp. 66-71.
International Search Report and Written Opinion mailed Jul. 11, 2012 in corresponding International Application No. PCT/US2012/035203.
International Search Report and Written Opinion mailed Jul. 30, 2012 in corresponding International Application No. PCT/US2012/035273.
Tracy J. Benson et al., "Cellulose Based Adsorbent Materials for the Dehydration of Ethanol Using Thermal Swing Adsorption", Adsorption, vol. 11, 2005, pp. 697-701.
Yang et al., Process of Ethanol Synthesis through esterification of acetic acid and economic analysis. No. 4, 2011, 15 Pages.
International Search Report and Written Opinion for PCT/US2011/042646 mailed on Feb. 23, 2012.
Office Action for corresponding Chinese Appl. No. 201180012654 dated Jan. 10, 2014.

\* cited by examiner

LIQUID ESTERIFICATION FOR THE PRODUCTION OF ALCOHOLS

CROSS REFERENCE TO RELATED APPLICATIONS

This application claims priority to U.S. Provisional App. No. 61/363,056, filed on Jul. 9, 2010, the entire contents and disclosures of which are incorporated herein by reference.

FIELD OF THE INVENTION

The present invention relates generally to production of ethanol and, in particular, to processes for esterifying a liquid stream derived from the crude ethanol product to improve ethanol recovery efficiencies.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition, when conversion is incomplete, unreacted acetic acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

EP02060555 describes a process for esterifying ethanoic acid and an alcohol to form ethanoates. The ethanoates are hydrogenated to produce ethanol.

The need remains for improving the recovery of ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol, comprising hydrogenating acetic acid from an acetic acid feedstream in a first reactor to produce a crude product; removing one or more non-condensable gases from the crude product to yield a liquid stream; reacting acetic acid and ethanol in the liquid stream in a second reactor to produce an ester enriched stream comprising ethanol and ethyl acetate; and recovering ethanol from the ester enriched stream. The operating temperature of the first reactor is from 125° C. to 350° C. and the operating temperature of the second reactor is lower than the first reactor and may be from 10° C. to 150° C.

In a second embodiment, the present invention is directed to a process for producing ethanol, comprising providing a crude ethanol product comprising ethanol, ethyl acetate, non-condensable gases, and acetic acid; removing one or more non-condensable gases from the crude product to yield a liquid stream; reacting acetic acid and ethanol in the liquid stream to produce an ester enriched stream comprising ethanol and ethyl acetate; and recovering ethanol from the ester enriched stream.

In a third embodiment, the present invention is directed to a process for producing ethanol, comprising hydrogenating acetic acid from an acetic acid feedstream in a first reactor to produce a crude ethanol product; separating a portion of crude ethanol product to produce an aqueous stream comprising water and a liquid crude ethanol product stream; reacting acetic acid and ethanol in the liquid crude ethanol product stream in a second reactor to produce an ester enriched stream; and recovering ethanol from the ester enriched stream.

In a fourth embodiment, the present invention is directed to a process for producing ethanol, comprising providing a crude ethanol product comprising ethanol, ethyl acetate, water, and acetic acid; separating a portion of crude ethanol product to produce an aqueous stream comprising water and a liquid crude ethanol product stream; reacting acetic acid and ethanol in the liquid crude ethanol product stream to produce an ester enriched stream; and recovering ethanol from the ester enriched stream.

BRIEF DESCRIPTION OF DRAWINGS

The invention is described in detail below with reference to the appended drawings, wherein like numerals designate similar parts.

DETAILED DESCRIPTION OF THE INVENTION

Introduction

The present invention relates to processes for recovering ethanol produced by hydrogenating acetic acid in the presence of a catalyst. The ethanol is recovered from a crude ethanol product comprising a mixture of ethanol, unreacted acetic acid, and optionally ethyl acetate, and impurities such as acetaldehyde and one or more acetals. The concentration of unreacted acetic acid in the mixture may vary depending on acetic acid conversion during the hydrogenation reaction. Separating the unreacted acetic acid from the crude reaction mixture requires additional energy. To improve recovery of ethanol, in one embodiment, the present invention includes a step of esterifying unreacted acetic acid contained in the crude ethanol product, in liquid phase, to reduce the concentration of the unreacted acetic acid, and thus increase the total conversion of acetic acid. In this manner, since less acetic acid will be contained the resulting crude ethanol composition, the energy requirements for ethanol recovery may be advantageously reduced.

The hydrogenation reaction is preferably conducted in the vapor phase, and the crude ethanol product is condensed into a liquid stream (which also may be referred to as a crude ethanol product). In preferred embodiments, light components such as residual hydrogen are removed from the crude ethanol product as a vapor stream. In processes according to the present invention, the liquid stream, optionally after removal of the vapor stream as discussed above, is esterified in a secondary reactor comprising an esterification catalyst, preferably an acid catalyst. Optionally, the liquid stream is esterified in a secondary reactor along with a recycled portion of the recovered ethanol. In another embodiment, a majority of the water is removed from the liquid stream prior to esterification.

Even at relative high conversions in the hydrogenation reaction, e.g., greater than 90 wt. %, there still may be a significant amount of unreacted acetic acid present in the crude ethanol product. Increasing conversion, although possible, may not reduce the amount of unreacted acid to a desired level. For purposes of the present invention, the term "conversion" refers to the amount of acetic acid in the feed that is converted to a compound other than acetic acid. Conversion is expressed as a mole percentage based on acetic acid in the feed. Selectivity is expressed as a mole percent based on converted acetic acid. It should be understood that each compound converted from acetic acid has an independent selectivity and that selectivity is independent from conversion. Surprisingly and unexpectedly, esterifying the unreacted acid, along with a minor portion of the ethanol, allows improved recovery of ethanol and reduces overall energy requirements.

Liquid Esterification

Figure 1:
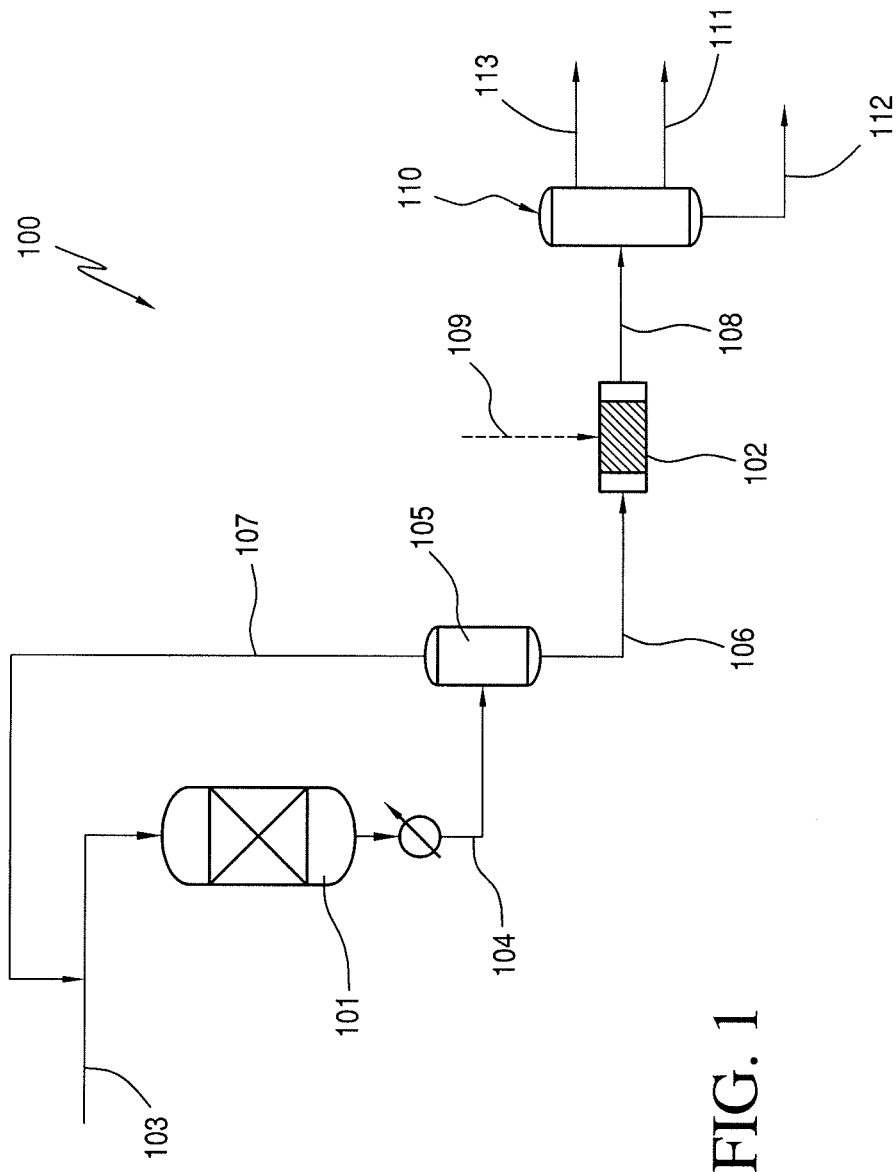
FIG. 1 is a schematic diagram of a reaction system having a liquid esterification reactor in accordance with one embodiment of the present invention.

FIG. 1 shows a reaction system 100 according to one embodiment of the present invention that comprises a hydrogenation reactor 101 and a secondary esterification reactor 102. An acetic acid feedstream 103 comprising acetic acid and hydrogen is directed to hydrogenation reactor 101. Reactor 101 produces a crude ethanol product 104 that is condensed and then separated in flasher 105 into a liquid stream 106 (a liquid crude ethanol product) and a vapor stream 107. Vapor stream 107 may be returned to reactor 101. Liquid stream 106 may comprise unreacted acetic acid depending on the acetic acid conversion. Preferably the conversion of acetic acid is greater than 60%, e.g., greater than 80%, greater than 90% or greater than 95%. Of course, in order to conduct the desired esterification reaction, some amount of unreacted acetic acid should be present in the crude ethanol product. In one embodiment, liquid stream 106 may comprise less than 40 wt. % unreacted acetic acid, e.g., less than 20 wt. % or less than 10 wt. %. In terms of ranges, liquid stream 106 may comprise from 1 to 40 wt. % unreacted acetic acid, e.g., from 3 to 35 wt. %, or from 5 to 20 wt. %.

Liquid stream 106 is fed to esterification reactor 102. In esterification reactor 102 unreacted acetic acid preferably reacts with ethanol to form ethyl acetate, thus yielding an ester enriched stream 108. Ester enriched stream 108 comprises more ethyl acetate than liquid stream 106, e.g., at least 5 wt. % more ethyl acetate, at least 10 wt. % more ethyl acetate, or at least 20 wt. % more ethyl acetate. In addition, ester enriched stream 108 preferably comprises less acetic acid than liquid stream 106. In one embodiment, ester enriched stream 108 comprises less than 10 wt. % unreacted acetic acid, e.g., less than 5 wt. % or less than 1 wt. %. In terms of ranges, ester enriched stream 108 may comprise from 0.01 to 10 wt. % unreacted acetic acid, e.g., from 0.05 to 5 wt. %, or from 0.05 to 1 wt. %. As a result of esterification, the total conversion of acetic acid in both reactors 101 and 102, may be greater than 90%, e.g., greater than 95% or greater than 99%.

Exemplary compositional ranges for ester enriched stream 108 in FIG. 1 are provided in Table 1.

TABLE 1

| ESTER ENRICHED STREAM (FIG. 1) | | | |
|---|---|---|---|
| | Conc. (wt. %) | Conc. (wt. %) | Conc. (wt. %) |
| Ethanol | 5 to 70 | 10 to 60 | 15 to 50 |
| Acetic Acid | <10 | 0.05 to 5 | 0.05 to 1 |
| Water | 5 to 35 | 5 to 30 | 10 to 30 |
| Ethyl Acetate | <30 | 0.001 to 20 | 1 to 10 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Alcohols | <8 | <0.1 | <0.05 |
| Other Esters | <5 | <0.005 | <0.001 |
| Other Ethers | <5 | <0.005 | <0.001 |

The amounts indicated as less than (<) in the tables throughout present application are preferably not present and if present may be present in trace amounts or in amounts greater than 0.0001 wt. %.

Embodiments of the present invention reduce unreacted acetic acid concentration without a large penalty to overall ethanol yields. Preferably, the unreacted acetic acid concentration is reduced from liquid stream 106 to ester enriched stream 108 by at least 40%, e.g., at least 50%, at least 75%, or at least 85%. These reductions, however, are coupled with a minor penalty in ethanol production. Preferably, overall ethanol production is reduced by less than 10%, e.g., less than 5%, or less than 2% relative to the same system but without an esterification unit. Although larger ethanol reductions may be possible, it is generally not desired to reduce unreacted acid concentrations at the expense of significant ethanol reductions.

As shown, ester enriched stream 108 is fed to distillation zone 110 to recover an ethanol product stream 111. In some embodiments, water stream 112, and/or lights stream 113 may also be separated from ester enriched stream 108. Preferably, water stream 112 comprises any remaining unreacted acetic acid, which may be further reacted by esterification, neutralized, and/or separated from the water stream 112. The lights stream 113, which may comprise ethyl acetate, may be recycled to reactor 101. Advantageously, in some embodiments of the present invention, improved efficiencies may be realized in recovering ethanol product stream 111 from distillation zone 110, because it is unnecessary to remove residual acetic acid, or, if residual acetic acid is present, less energy is required to remove the residual acetic acid because of its reduced concentration.

Lower conversions of acetic acid in the hydrogenation reactor are less preferred, e.g., less than 80%. In some embodiments, an ethanol feed 109 may be fed to secondary esterification reactor 102 when there is a lower acetic acid conversion. Ethanol feed 109 is preferably taken from ethanol product stream 111. In one embodiment, up to 50% of the ethanol from ethanol product stream 111 is recycled as ethanol feed 109, and more preferably up to 10%. In terms of ranges, from 1 to 50% of the ethanol from ethanol product stream 111 may be recycled as ethanol feed 109, and more preferably from 5 to 10%. The presence of additional ethanol in secondary esterification reactor 102 may allow an even further reduction of unreacted acetic acid through esterification with ethanol.

In other embodiments, optional ethanol feed 109 may be used with higher conversion of acetic acid in reactor 101, e.g., where conversion is greater than 80%, e.g., greater than 90%, or greater than 95%.

When optional ethanol feed 109 is used, the ester enriched stream 108 may also comprise more ethanol than liquid stream 106. The additional ethanol will vary depending on the amount of ethanol that is fed to secondary esterification reactor 102 via ethanol feed 109, and ester enriched stream 108 may contain more than 70 wt. % ethanol.

Figure 2:
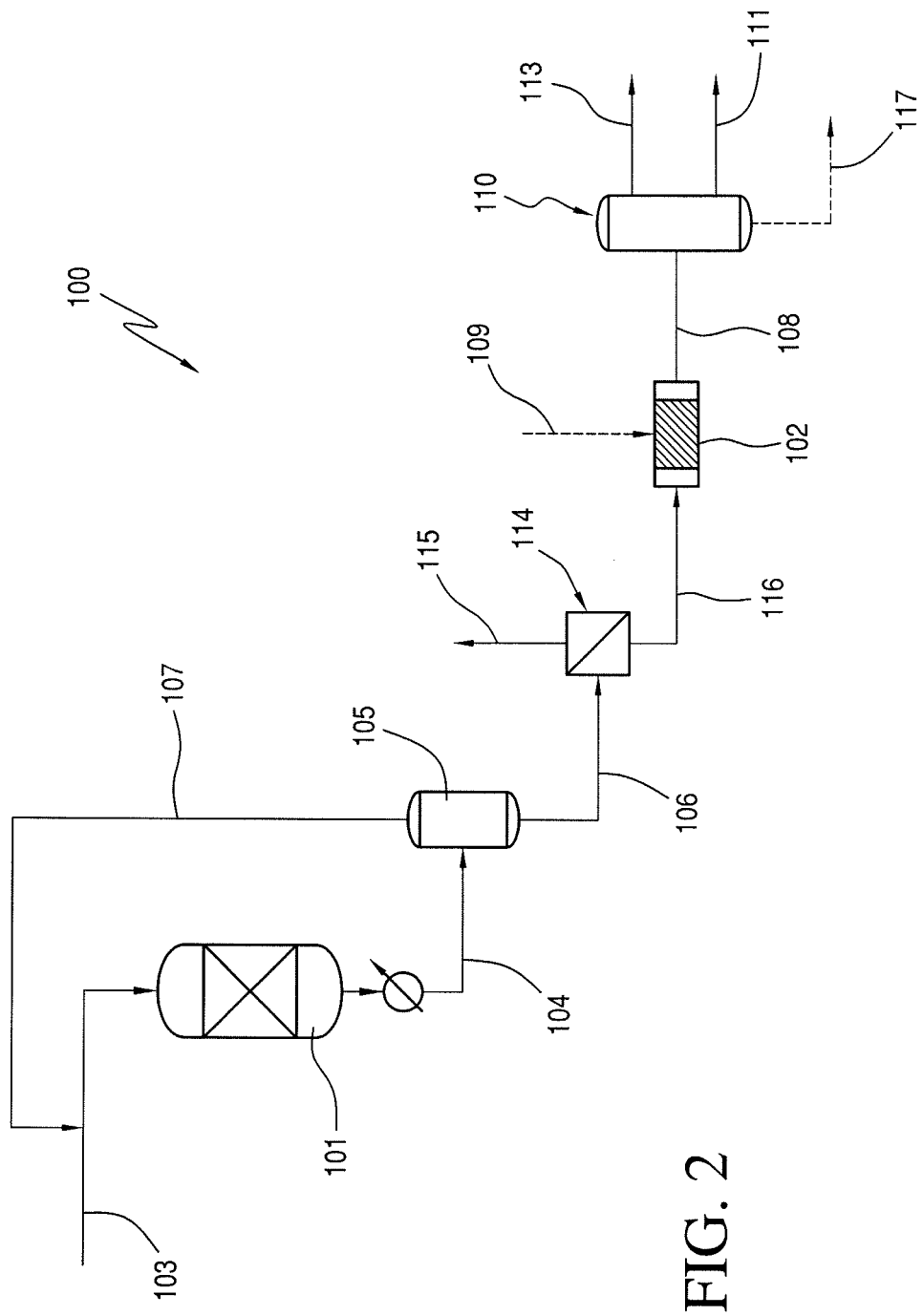
FIG. 2 is a schematic diagram of a reaction system that removes water prior to esterification in accordance with one embodiment of the present invention.

FIG. 2 shows another embodiment in which a majority of the water in liquid stream 106 is removed prior to the secondary esterification reactor 102. One or more membranes 114 are shown in FIG. 2, which remove water as the permeate 115, and the remaining portion of liquid stream forms retentate 116. The membrane may comprise a polymeric membrane, for example, comprising polyimide hollow fibers. Alternatively, the membrane may be a zeolite membrane or a hybrid membrane with both organic and inorganic components. Suitable membranes also include shell and tube membrane modules having one or more porous material elements therein. Non-porous material elements may also be included. The material elements may comprise a polymeric element such as polyvinyl alcohol, cellulose esters, and perfluoropolymers. Membranes that may be employed in embodiments of the present invention include those described in Baker, et al., "Membrane separation systems: recent developments and future directions," (1991) pages 151-169, and Perry et al., "Perry's Chemical Engineer's Handbook," $7^{th}$ ed. (1997), pages 22-37 to 22-69, the entire contents and disclosures of which are hereby incorporated by reference. Retentate 116 is fed to secondary esterification reactor 102. In some embodiments, a pervaporation unit may be used in place of or in addition to the membranes 114.

The amount of water removed prior to introduction into esterification reactor 102 may vary, but generally membranes 114 may be capable of removing at least 50% of the water in liquid stream 106, e.g., at least 75% or at least 85%. Although complete removal of water may be feasible, it is generally more preferred to remove from about 75% to 99% of the water from liquid stream 106. Removing water from liquid stream 106 advantageously allows the equilibrium in secondary esterification reactor 102 to consume additional unreacted acetic acid. Using an initial water removal step yields an ester enriched stream 108 that may comprise less than 5 wt. % unreacted acetic acid, e.g., less than 3 wt. % or less than 0.5 wt. %. In terms of ranges, ester enriched stream 108 in FIG. 2 may comprise from 0.001 to 5 wt. % unreacted acetic acid, e.g., from 0.001 to 3 wt. %, or from 0.005 to 0.5 wt. %.

Exemplary compositional ranges for ester enriched stream 108 having reduced water according to FIG. 2 are provided in Table 2.

TABLE 2

ESTER ENRICHED STREAM (FIG. 2)

|  | Conc. (wt. %) | Conc. (wt. %) | Conc. (wt. %) |
| --- | --- | --- | --- |
| Ethanol | 5 to 85 | 10 to 80 | 15 to 75 |
| Acetic Acid | <5 | 0.01 to 3 | 0.001 to 0.5 |
| Water | <20 | 0.001 to 10 | 0.01 to 5 |
| Ethyl Acetate | <25 | 0.001 to 20 | 1 to 15 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Alcohols | <8 | <0.1 | <0.05 |
| Other Esters | <5 | <0.005 | <0.001 |
| Other Ethers | <5 | <0.005 | <0.001 |

Although one membrane is shown in FIG. 2, it should be appreciated that an array of membranes may be used in a multistep configuration to remove more water, optionally a majority of the water from liquid stream 106. Preferably, the membranes are acid-resistant membranes that selectively permeate water.

In FIG. 2, ester enriched stream 108 is fed to distillation zone 110 to recover an ethanol product stream 111. In some embodiments, lights stream 113 may also be separated from ester enriched stream 108. The lights stream 113, which may comprise ethyl acetate, may be recycled to reactor 101. Optionally, a residue stream 117 may be taken from distillation zone. Residue stream 117 may comprise any remaining acetic acid and/or water. In preferred embodiments, it may not be necessary to separate residue stream 117. When separated, residue stream may comprise acetic acid that may be further reacted by esterification, neutralized, and/or separated from the residue stream. Advantageously, as discussed above, in some embodiments of the present invention, improved efficiencies may be realized in recovering ethanol product stream 111 from distillation zone 110, because it is unnecessary to remove residual acetic acid, or, if residual acetic acid is present, less energy is required to remove the residual acetic acid because of its reduced concentration.

The esterification reaction preferably is carried out in the liquid phase at a reaction temperature that ranges from 10° C. to 150° C., e.g., from 20° C. to 100° C., or from 30° C. to 80° C. In one embodiment, the esterification reaction is conducted at a temperature that is less than the hydrogenation reaction temperature. The pressure in the esterification is generally atmospheric, but may vary depending on the hydrogenation reaction pressure and generally ranges from 10 kPa to 2000 kPa, e.g., from 50 kPa to 1000 kPa, or from 100 kPa to 500 kPa.

Acid-catalyzed esterification reactions may be used with some embodiments of the present invention. The catalyst should be thermally stable at reaction temperatures. Suitable catalysts may be solid acid catalysts comprising an ion exchange resin, zeolites, Lewis acid, metal oxides, inorganic salts and hydrates thereof, and heteropoly acid and salts thereof Silica gel, aluminum oxide, and aluminum phosphate are also suitable catalysts. Acid catalysts include, but are not limited to, sulfuric acid, and tosic acid. In addition, Lewis acids may also be used as esterification catalysts, such as scandium(III) or lanthanide(III) triflates, hafnium(IV) or zirconium(IV) salts, and diarylammonium arenesulfonates. The catalyst may also include sulfonated (sulphonic acid) ion-exchange resins (e.g., gel-type and macroporous sulfonated styrene-divinyl benzene IERs), sulfonated polysiloxane resins, sulfonated perfluorinated (e.g., sulfonated poly-perfluoroethylene), or sulfonated zirconia.

Hydrogenation of Acetic Acid

The process of the present invention may be used with any acetic acid hydrogenation process for producing ethanol. The materials, catalyst, reaction conditions, and separation are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The operating temperatures of the hydrogenation reactor is generally higher than the esterification reactor. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIB, VIIB, VIII transitional metals, a lanthanide metal, an actinide metal, or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. Most preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another, or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from both the first and second metals. In preferred embodiments, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal is preferably from 0.05 to 4 wt. %, e.g., from 0.1 to 3 wt. %, or from 0.1 to 2 wt. %.

In addition to one or more metals, in some embodiments of the present invention, the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include siliceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

The catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiments, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. The basic support modifier may be selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain NorPro. The Saint-Gobain NorPro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry; and packing density of about 0.352 $g/cm^3$ (22 $lb/ft^3$).

A preferred silica/alumina support material is KA-160 silica spheres from Süd-Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

The conversion of the hydrogenation reaction may be at least 10%, e.g., at least 20%, at least 40%, at least 50%, at least 60%, at least 70% or at least 80%. Although catalysts that have high conversions are desirable, such as at least 80% or at least 90%, in some embodiments, a low conversion may be acceptable at high selectivity for ethanol. In particular embodiments, low conversion may be used in either reactor when hydrogenation reactors are staged.

Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 per grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 40 wt. % water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 50 | 15 to 70 | 20 to 70 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product comprises acetic acid in an amount less than 20 wt. %, e.g., less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Ethanol Recovery

Figure 3:
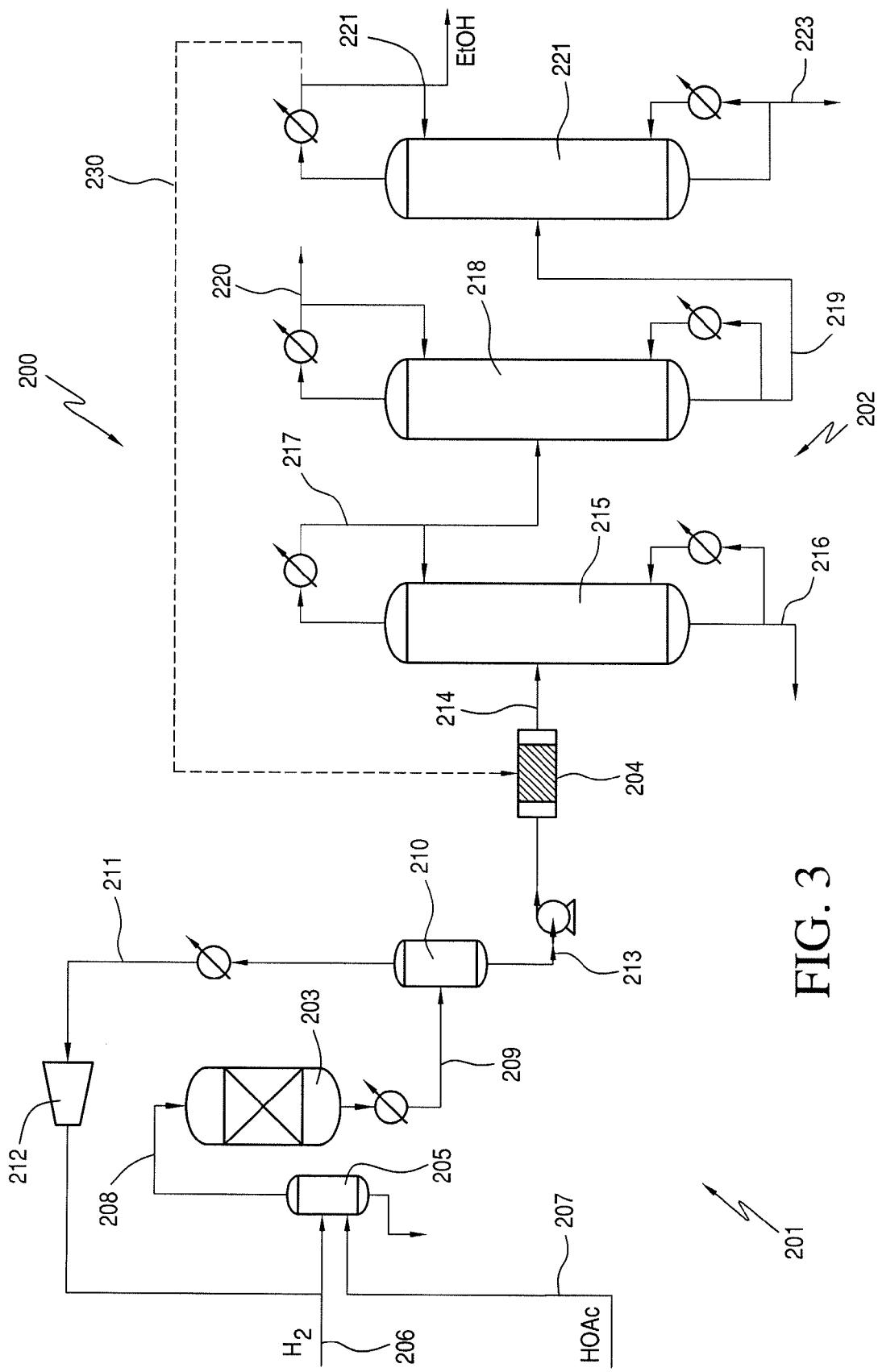
FIG. 3 is a schematic diagram of a hydrogenation system in accordance with one embodiment of the present invention.

An exemplary hydrogenation system 200 is shown in FIG. 3. System 200 comprises reaction zone 201 and distillation zone 202. System 200 also comprises an hydrogenation reactor 203 and a secondary esterification reactor 204.

In reaction zone 201, hydrogen and acetic acid are fed to a vaporizer 205 via lines 206 and 207 respectively, to create a vapor feed stream in line 208 that is directed to hydrogenation reactor 203. In one embodiment, lines 206 and 207 may be combined and jointly fed to the vaporizer 205. The temperature of the vapor feed stream in line 208 is preferably from 100° C. to 350° C., e.g., from 120° C. to 310° C. or from 150° C. to 300° C. Any feed that is not vaporized is removed from vaporizer 205, as shown in FIG. 3, and may be recycled or discarded thereto. In addition, although FIG. 3 shows line 208 being directed to the top of reactor 203, line 208 may be directed to the side, upper portion, or bottom of reactor 203. Further modifications and additional components to reaction zone 202 are described below.

Reactor 203 contains the catalyst that is used in the hydrogenation of the carboxylic acid, preferably acetic acid. In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In certain embodiments of the invention, the guard bed media is functionalized to trap particular species such as sulfur or halogens. During the hydrogenation process, a crude ethanol product is withdrawn, preferably continuously, from reactor 203 via line 209.

Crude ethanol product 209 may be condensed and fed to flasher 210, which, in turn, provides a vapor stream and a liquid stream. The flasher 210 may operate at a temperature of from 50° C. to 250° C., e.g., from 30° C. to 225° C. or from 60° C. to 200° C. The pressure of flasher 210 may be from 50 kPa to 2000 kPa, e.g., from 75 kPa to 1500 kPa or from 100 to 1000 kPa.

The vapor stream exiting the flasher 210 may comprise hydrogen, hydrocarbons, and other non-condensable gases, which may be purged and/or returned to reaction zone 201 via line 211. As shown in FIG. 3, the returned portion of the vapor stream passes through compressor 212 and is combined with the hydrogen feed 206 and co-fed to vaporizer 205.

Optionally, crude ethanol product 209 may pass through one or more membranes to separate hydrogen and/or other non-condensable gases.

The liquid in line 213 from flasher 210 is fed to esterification reactor 204. Esterification reactor 204 contains a suitable acidic catalyst for reacting unreacted acetic acid with ethanol to yield an ester enriched stream in line 214. Ester enriched stream 214 as indicated above comprises less than 10 wt. % unreacted acid and more preferably less than 1 wt. % unreacted acid.

Ester enriched stream in line 214 is fed to the side of first column 215, also referred to as an "dilute acid separation column." Exemplary compositions of line 214 are provided above in Table 1. It should be understood that ester enriched stream in line 214 may contain other components, not listed, such as additional components in the feed.

The system shown in FIG. 3 may also be used with an initial water removal step, as indicated above in FIG. 2. When used with initial water removal, ester enriched stream in line 214 may have the composition as indicated in Table 2. Further, it may not be necessary to feed ester enriched stream 214 to column 215, and ester enriched stream 214 instead may be fed directly to column 218.

In one embodiment, the concentration of unreacted acetic acid in line 214 may be from 0.01 to 10 wt. %, e.g., from 0.05 to 5 wt. %, or from 0.05 to 1 wt. %. As shown, line 214 is introduced in the lower part of first column 215, e.g., lower half or lower third. Column 215 operates to remove a dilute acid stream as residue 216. Dilute acid stream comprises water and less than 30 wt. % acetic acid. In one embodiment, residue 216 may be separated into a water stream and an acetic acid stream, and either stream may be returned to reaction zone 201. In other embodiments, the residue 216 may be treated in a weak acid recovery system to recover acetic acid. In still other embodiments, residue 216 may be sent to a reactive distillation column to further convert residual acetic acid to esters, preferably by reacting with methanol to form methyl acetate. In other embodiments, residue 216 may be directed to a waste water treatment facility. Generally, the organic content, e.g., unreacted acid, of the residue may be suitable to feed microorganisms used to treat waste water.

The present invention allows for improved recovery of ethanol using less energy because line 214 contains reduced amounts of acetic acid. Thus, the residue 216, as well as distillate 217, of column 215 would contain minor amounts of acetic acid. In some embodiments, most of the water in line 214 may be withdrawn as the residue 216. Preferably, a majority of the water is withdrawn in residue via line 216 as opposed to distillate via line 217 such that the weight ratio of water in line 216 to line 217 is greater than 2:1.

First column 215 also forms an overhead distillate, which is withdrawn in line 217, and which may be condensed and refluxed, for example, at a ratio of from 10:1 to 1:10, e.g., from 3:1 to 1:3 or from 1:2 to 2:1.

In some embodiments, when the content of acetic acid in line 214 is less than 5 wt. %, the column 215 may be skipped and line 214 may be introduced directly to second column 218, also referred to herein as a "light ends column." In addition, column 215 may be operated to initially remove a substantial portion of water as the residue.

Any of columns 215, 218, or 221 may comprise any distillation column capable of separation and/or purification. The columns preferably comprise tray columns having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section and so on.

The associated condensers and liquid separation vessels that may be employed with each of the distillation columns may be of any conventional design and are simplified in FIG. 3. As shown in FIG. 3, heat may be supplied to the base of each column or to a circulating bottom stream through a heat exchanger or reboiler. Other types of reboilers, such as internal reboilers, may also be used in some embodiments. The heat that is provided to reboilers may be derived from any heat generated during the process that is integrated with the reboilers or from an external source such as another heat generating chemical process or a boiler. Although one reactor and one flasher are shown in FIG. 3, additional reactors, flashers, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in any of the columns may vary. As a practical matter, pressures from 10 kPa to 3000 kPa will generally be employed in these zones although in some embodiments subatmospheric pressures may be employed as well as superatmospheric pressures. Temperatures within the various zones will normally range between the boiling points of the composition removed as the distillate and the composition removed as the residue. It will be recognized by those skilled in the art that the temperature at a given location in an operating distillation column is dependent on the composition of the material at that location and the pressure of column. In addition, feed rates may vary depending on the size of the production process and, if described, may be generically referred to in terms of feed weight ratios.

When column 215 is operated under about 170 kPa, the temperature of the residue exiting in line 216 preferably is from 90° C. to 130° C., e.g., from 95° C. to 120° C. or from 100° C. to 115° C. The temperature of the distillate exiting in line 217 from column 215 preferably is from 60° C. to 90° C., e.g., from 65° C. to 85° C. or from 70° C. to 80° C. In other embodiments, the pressure of first column 215 may range from 0.1 kPa to 510 kPa, e.g., from 1 kPa to 475 kPa or from 1 kPa to 375 kPa. Distillate and residue compositions for first column 215 for one exemplary embodiment of the present invention are provided in Table 4. In addition, for convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 4

| FIRST COLUMN | | | |
|---|---|---|---|
| | Conc. (wt. %) | Conc. (wt. %) | Conc. (wt. %) |
| Distillate | | | |
| Ethanol | 20 to 90 | 30 to 85 | 50 to 85 |
| Water | 4 to 38 | 7 to 32 | 7 to 25 |
| Acetic Acid | <1 | 0.001 to 1 | 0.01 to 0.5 |
| Ethyl Acetate | <60 | 5 to 40 | 8 to 45 |
| Acetaldehyde | <10 | 0.001 to 5 | 0.01 to 4 |
| Acetal | <4.0 | <3.0 | <2.0 |
| Acetone | <0.05 | 0.001 to 0.03 | 0.01 to 0.025 |
| Residue | | | |
| Acetic Acid | <70 | 0.01 to 55 | 0.05 to 30 |
| Water | 30 to 100 | 45 to 97 | 60 to 95 |
| Ethanol | <1 | <0.9 | <0.5 |

As indicated in Table 4, embodiments of the present invention allow a majority of the water to be withdrawn in residue line 216. In addition, this approach results in a reduction in the amount of acetic acid that may be carried over in the distillate line 217. Preferably, there is substantially no or very low amounts of acetic acid in distillate line 217. Reducing acetic acid in distillate 217 advantageously may reduce the amount of acetic acid in the final ethanol product and reduces overall energy requirements in the separation steps.

Some species, such as acetals, may decompose in column 215 to low or even undetectable amounts. In addition, to esterification reactor 204, there may also be an equilibrium reaction after the crude ethanol product 209 exits hydrogenation reactor 203 and prior to secondary esterification reactor 204. Generally, the reaction may occur in line 213. Depending on the concentration of acetic acid, equilibrium may be driven towards formation of ethyl acetate. The equilibrium may be regulated using the residence time and/or temperature of liquid stream 213.

The distillate, e.g., overhead stream, of column 215 optionally is condensed and refluxed as shown in FIG. 3, preferably, at a reflux ratio of 1:5 to 10:1. The distillate in line 217 preferably comprises ethanol, ethyl acetate, and lower amounts of water.

The first distillate in line 217 is introduced to the second column 218, also referred to as a "light ends column," preferably in the top part of column 218, e.g., top half or top third. Second column 218 may be a tray column or packed column. In one embodiment, second column 218 is a tray column having from 5 to 70 trays, e.g., from 15 to 50 trays, or from 20 to 45 trays. As one example, when a 30 tray column is used in a column without water extraction, line 117 is introduced at tray 2. In another embodiment, the second column 218 may be an extractive distillation column. In such an embodiment, an extraction agent, such as water, may be added to second column 218. If the extraction agent comprises water, it may be obtained from an external source or from an internal return/recycle line from one or more of the other columns. Other suitable extractive agents that may be used include dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or combinations thereof.

In some embodiments, a portion of the water in first distillate 217 may be removed prior to second column 218, using one or more membranes, and/or adsorptions units.

Although the temperature and pressure of second column 218 may vary, when at about 20 kPa to 70 kPa, the temperature of the second residue exiting in line 219 preferably is from 30° C. to 75° C., e.g., from 35° C. to 70° C. or from 40° C. to 65° C. The temperature of the second distillate exiting in line 220 from second column 218 preferably is from 20° C. to 55° C., e.g., from 25° C. to 50° C. or from 30° C. to 45° C. Second column 218 may operate at a reduced pressure near or at vacuum conditions, to further favor separation of ethyl acetate and ethanol. In other embodiments, the pressure of second column 218 may range from 0.1 kPa to 510 kPa, e.g., from 1 kPa to 475 kPa or from 1 kPa to 375 kPa. Exemplary distillate and residue compositions for second column 218 are provided in Table 5 below. It should be understood that the distillate and residue may also contain other components, not listed, such as additional components in the feed.

TABLE 5

SECOND COLUMN

|  | Conc. (wt. %) | Conc. (wt. %) | Conc. (wt. %) |
|---|---|---|---|
| Distillate |  |  |  |
| Ethyl Acetate | 5 to 90 | 10 to 80 | 15 to 75 |
| Acetaldehyde | <60 | 1 to 40 | 1 to 35 |
| Ethanol | <45 | 0.001 to 40 | 0.01 to 35 |
| Water | <20 | 0.01 to 10 | 0.1 to 5 |
| Residue |  |  |  |
| Ethanol | 40 to 99.5 | 50 to 95 | 60 to 90 |
| Water | <60 | 0.5 to 50 | 0.1 to 30 |
| Ethyl Acetate | <1 | 0.001 to 2 | 0.001 to 0.5 |
| Acetic Acid | <0.5 | <0.01 | 0.001 to 0.01 |

The weight ratio of ethanol in the second residue to ethanol in the second distillate preferably is at least 2:1, e.g., at least 6:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. In embodiments that use an extractive column with water as an extraction agent as the second column 108, the weight ratio of ethyl acetate in the second residue to ethyl acetate in the second distillate is less than 0.1:1.

Returning to the second distillate, which comprises ethyl acetate and/or acetaldehyde, the second distillate preferably is refluxed as shown in FIG. 3, for example, at a reflux ratio of from 1:30 to 30:1, e.g., from 1:5 to 5:1 or from 1:3 to 3:1. In some embodiments, the second distillate in line 220 or portion thereof may be returned reactor 203. For example, it may be advantageous to return a portion of second distillate 220 to reactor 203. In certain embodiments and as shown in FIG. 3, the second distillate may be fed to an acetaldehyde removal column to recover aldehyde that may be recycled to the reactor 203. This column may also separate the second distillate 220 to yield a residue, which comprises ethyl acetate. In other embodiments, the second distillate may be hydrolyzed or fed to an hydrogenolysis reactor (not shown) to produce ethanol from ethyl acetate. In still other embodiments, the second distillate may be purged from system.

Optionally, when second distillate 217 comprises water, the water may be removed using one or more membranes, and/or adsorptions units. The removed water may be purged or retained in the system.

The second residue 219 from the bottom of second column 218 comprises ethanol and water. Depending on the concentration of water in second residue 219, the water may be removed to yield an ethanol product. In some embodiments, the amount of water in residue 219 may be sufficient for the particular use of the ethanol product, such as for industrial uses. For uses that require lower amounts of water, in particular as fuels, the water may be removed using a distillation column, membrane, adsorption unit, or combination thereof.

As shown in FIG. 3, second residue is fed via line 219 to third column 221, also referred to as a "product column." The second residue in line 219 is introduced in the lower part of third column 221, e.g., lower half or lower third. Third column 109 recovers ethanol, which preferably is substantially pure other than the azeotropic water content, as the distillate in line 222. The distillate of third column 221 preferably is refluxed as shown in FIG. 3, for example, at a reflux ratio of from 1:10 to 10:1, e.g., from 1:3 to 3:1 or from 1:2 to 2:1. The third residue in line 223, which preferably comprises primarily water, may be returned as an extractive agent to another column, such as the second column 218. In some embodiments, third residue may be used to hydrolyze an ethyl acetate stream, such as the second distillate 220. Third column 221 is preferably a tray column as described above and preferably operates at atmospheric pressure. The temperature of the third distillate exiting in line 222 from third column 221 preferably is from 60° C. to 110° C., e.g., from 70° C. to 100° C. or from 75° C. to 95° C. The temperature of the third residue 223 exiting from third column 221 preferably is from 70° C. to 115° C., e.g., from 80° C. to 110° C. or from 85° C. to 105° C., when the column is operated at atmospheric pressure. Exemplary components of the distillate and residue compositions for third column 222 are provided in Table 6 below. It should be understood that the distillate and residue may also contain other components, not listed, such as components in the feed.

TABLE 6

THIRD COLUMN

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns 215, 218 and/or 221 in the system 200. Preferably at least one side stream is used to remove impurities from the third column 221. The impurities may be purged and/or retained within the system 200.

Optionally, a portion of the third distillate 222, e.g., up to 50% of the third distillate, may be withdrawn via line 230 and fed to esterification reactor 204.

The ethanol product is taken from the third distillate 222. Third distillate 222 may be further purified to form an anhydrous ethanol product stream, i.e., "finished anhydrous ethanol," using one or more additional separation systems, such as, for example, distillation columns (e.g., a finishing column), membranes, adsorption units, or molecular sieves. Anhydrous ethanol may be suitable for fuel applications.

The ethanol product may be an industrial grade ethanol preferably comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 7.

TABLE 7

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol is from 80 to 1,000 wppm, e.g., from 95 to 1,000 wppm, from 100 to 700 wppm, or from 150 to 500 wppm. In one embodiment, the finished ethanol composition preferably is substantially free of acetaldehyde and may comprise less than 8 wppm of acetaldehyde, e.g., less than 5 wppm or less than 1 wppm.

In some embodiments, when further water separation is used, the ethanol product may be withdrawn as a stream from the water separation unit, such as an adsorption unit, membrane and/or molecular sieve. In such embodiments, the ethanol concentration of the ethanol product may be higher than indicated in Table 7, and preferably is greater than 97 wt. % ethanol, e.g., greater than 98 wt. % or greater than 99.5 wt. %, and less than 3 wt. % water, e.g. less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid or reacted with polyvinyl acetate. The finished ethanol composition may be dehydrated to produce ethylene. Any of known dehydration catalysts can be employed in to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference.

In order that the invention disclosed herein may be more efficiently understood, an example is provided below. The following examples describe the various distillation processes of the present invention.

EXAMPLES

Example 1

Acetic acid and hydrogen are fed to a hydrogenation reactor having a catalyst that converts about 95% of the acetic acid and has a selectivity to ethanol of about 78%. The reactor effluent comprises 5 wt. % unreacted acetic acid, 52.9 wt. % ethanol, 13.2 wt. % ethyl acetate, and 26.9 wt. % water. The reactor effluent is sent to a flasher to separate a liquid stream.

Example 2

The liquid stream from Example 1 is fed to an esterification reactor under similar conditions. The catalyst for the esterification is an Amberlyst™ 15 and the esterification is conducted at a temperature of 60° C. at atmospheric pressure. An ester enriched stream is withdrawn from esterification reactor. The ester enriched stream comprises 2.5 wt. % unreacted acetic acid, 50.8 wt. % ethanol, 16.9 wt. % ethyl acetate, and 27.8 wt. % water. The acetic acid conversion in the esterification reactor was 50.5%, which provided a total acid conversion of 97.5%.

Example 3

The liquid stream from Example 1 along with an ethanol recycle stream is fed to an esterification reactor under similar conditions. The ethanol recycle stream comprises 10% of the ethanol recovered by further separation. An ester enriched stream is withdrawn from esterification reactor. The ester enriched stream comprises 2.2 wt. % unreacted acetic acid, 53.3 wt. % ethanol, 16.3 wt. % ethyl acetate, and 26.4 wt. % water. The acetic acid conversion in the esterification reactor was 54.3%, which provided a total acid conversion of 97.7%.

Example 4

The liquid stream from Example 1 along with an ethanol recycle stream is fed to an esterification reactor under similar conditions. The ethanol recycle stream comprises 50% of the ethanol recovered by further separation. An ester enriched stream is withdrawn from esterification reactor. The ester enriched stream comprises 1.4 wt. % unreacted acetic acid, 60.9 wt. % ethanol, 14.1 wt. % ethyl acetate, and 22.1 wt. % water. The acetic acid conversion in the esterification reactor was 64.7%, which provided a total acid conversion of 98.2%.

Example 5

The liquid stream from Example 1 is fed to one or more membranes to remove about 95% of the water under similar conditions. The liquid stream having a reduced water content is fed to an esterification reactor. An ester enriched stream is withdrawn from esterification reactor. The ester enriched stream comprises 0.4 wt. % unreacted acetic acid, 66.3 wt. % ethanol, 27.0 wt. % ethyl acetate, and 3.7 wt. % water. The acetic acid conversion in the esterification reactor was 94.0%, which provided a total acid conversion of 99.7%.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol comprising:
    hydrogenating acetic acid from an acetic acid feedstream in a first reactor to produce a crude product;
    removing one or more non-condensable gases from the crude product to yield a liquid stream;
    reacting the acetic acid and ethanol of the liquid stream in a second reactor, under esterification conditions, to produce an ester enriched stream comprising ethanol and ethyl acetate; and
    recovering ethanol from the ester enriched stream, wherein the ester enriched stream comprises less than 10 wt. % acetic acid.

2. The process of claim 1, wherein at least a portion of the recovered ethanol is added to the second reactor.

3. The process of claim 1, wherein the liquid stream comprises less than 40 wt. % acetic acid.

4. The process of claim 1, wherein the ester enriched stream comprises 0.01 wt. % to 10 wt. % acetic acid.

5. The process of claim 1, further comprising providing an alcohol stream to the second reactor.

6. The process of claim 5, wherein the alcohol stream comprises less than 50 wt. % of the recovered ethanol.

7. The process of claim 1, wherein the conversion of acetic acid in the second reactor is greater than 40%.

8. The process of claim 1, wherein the total conversion of acetic acid in the first and second reactor is greater than 90%.

9. The process of claim 1, wherein the first reactor comprises a different catalyst than the second reactor.

10. The process of claim 1, wherein the first reactor comprises a hydrogenation catalyst selected from the group consisting of platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron.

11. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

12. The process of claim 1, wherein the second reactor comprises an acid catalyst.

13. The process of claim 1, wherein the first reactor operates a temperature from 125° C. to 350° C. and the second reactor operates a temperature from 10° C. to 150° C., wherein the operating temperature of the second reactor is lower than the operating temperature of the first reactor.

14. A process for producing ethanol comprising:
    providing a crude ethanol product comprising ethanol, ethyl acetate, non-condensable gases, and acetic acid;
    removing one or more non-condensable gases from the crude product to yield a liquid stream;
    reacting the acetic acid and ethanol of the liquid stream in a reactor, under esterification conditions, to produce an ester enriched stream comprising ethanol and ethyl acetate; and
    recovering ethanol from the ester enriched stream, wherein the ester enriched stream comprises less than 10 wt. % acetic acid.

15. A process for producing ethanol comprising:
    hydrogenating acetic acid from an acetic acid feedstream in a first reactor to produce a crude ethanol product;
    separating a portion of crude ethanol product to produce an aqueous stream comprising water and a liquid crude ethanol product stream;
    directing in the liquid crude ethanol product stream to a second reactor to react the acetic acid and the ethanol to produce an ester enriched stream; and
    recovering ethanol from the ester enriched stream, wherein the ester enriched stream comprises less than 10 wt. % acetic acid.

16. The process of claim 15, wherein the aqueous stream comprises at least 75% of the water from the crude product.

17. The process of claim 15, wherein the step of separating a portion of crude product is conducted by passing the portion of crude product through a membrane to yield a permeate comprising the aqueous stream and a retentate comprising the liquid crude ethanol product stream.

18. The process of claim 15, wherein the step of separating a portion of crude product is conducted by feeding the portion of crude product to a pervaporation unit.

19. The process of claim 15, wherein at least a portion of the recovered ethanol is added to the second reactor.

20. The process of claim 15, wherein the liquid crude ethanol product stream comprises less than 40 wt. % acetic acid.

21. The process of claim 15, wherein the ester enriched stream comprises from 0.01 wt. % to 10 wt. % acetic acid.

22. A process for producing ethanol comprising:
    providing a crude ethanol product comprising ethanol, ethyl acetate, water, and acetic acid;
    separating a portion of crude ethanol product to produce an aqueous stream comprising water and a liquid crude ethanol product stream;
    reacting the acetic acid and ethanol of the liquid crude ethanol product stream in a reactor, under esterification conditions, to produce an ester enriched stream; and
    recovering ethanol from the ester enriched stream.

* * * * *